United States Patent [19]

Lester et al.

[11] Patent Number: 5,747,278
[45] Date of Patent: May 5, 1998

[54] DNA ENCODING INWARD RECTIFIER, G-PROTEIN ACTIVATED, MAMMALIAN, POTASSIUM KGA CHANNEL AND USES THEREOF

[75] Inventors: Henry A. Lester; Nathan Dascal, both of South Pasadena; Nancy F. Lim, Pasadena; Wolfgang Schreibmayer, South Pasadena; Norman Davidson, Sierra Madre, all of Calif.

[73] Assignee: California Institute of Technology, Pasadena, Calif.

[21] Appl. No.: 66,371

[22] Filed: May 21, 1993

[51] Int. Cl.⁶ .................... C12N 15/12; C07K 38/17
[52] U.S. Cl. .............. 435/69.1; 435/325; 435/252.3; 435/254.11; 435/320.1; 536/23.5
[58] Field of Search .................... 536/23.5, 24.31; 435/69.1, 320.1, 240.2, 252.3, 254.11, 325

[56] References Cited

PUBLICATIONS

Brown, A.M. "Regulation of Heartbeat by G Protein–Coupled Ion Channels," *Am. J. Physiol.*, 259(6):H1621–H1628 (1990).
Kirsch, G.E. and A.M. Brown, "Trypsin Activation of Atrial Muscarinic K⁺ Channels," *Am. J. Pysiol.*, 26(1):H334–H338 (1989).
Adams, R.L.P., et al. (1981) *Biochemistry of the Nucleic Acids*, 9th ed., London: Chapman and Hall; p. 124.
Lesage, F., et al. (1994) *FEBS Lett.* 353: 37–42.
Adams, M.D., et al. (1992) GenBank Acc. No. M78731 (database record).
Sambrook, J., et al. (1989) *Molecular Cloning*, 2nd ed, New York: Cold Spring Harbor; Chap. 11.
Hemmings, B.A., et al. (1990) Biochem. 29:3166–73.
Dascal, N., et al. (1993) Proc. Natl. Acad. Sci. USA 90: 6596–600.
Dascal, N., et al (1993) Ibid. 90: 10235–39.
Sakmann, B. et al., "Acetylcholine activation of single muscarinic K⁺ channels in isolated pacemaker cells of the mammalian heart" *Nature* 303:250–253 (1983).
Yatani, A. et al., "Direct Activation of Mammalian Atrial Muscarnic Potassium Channels by GTP Regulatory Protein $G_k$," *Science* 235:207–211 (1987).
Kubo, Y. et al., "Primary structure and functional expression of a rat G–protein–coupled mascarinic potassium channel", *Nature* 364:802–806 (1993).
Alrich, R. "Advent of a new family", *Nature*, 362:107–108 (1993).
Ho, K. et al. (1993) "Cloning and expression of an inwardly rectifying ATP–regulated potassium channel", *Nature* 362:31–38.
Kubo, Y. et al. (1993) "Primary structure and functional expression of a mouse inward rectifier potassium channel", *Nature* 362:127–133.
Karschin, A. et al. (1991) "Heterologously expressed serotonin 1A receptors couple to muscarinic K⁺ channels in heart", *Proc. Natl. Acad. Sci. USA* 88:5694–5698.
Adams, M.D. et al. (1992) "Sequence identification of 2,375 human brain genes", *Nature* 355:632–634.

*Primary Examiner*—David L. Fitzgerald
*Attorney, Agent, or Firm*—Flehr Hohbach Test Albritton & Herbert LLP

[57] ABSTRACT

Nucleic acids encoding mammalian "KGA" potassium channels are provided. Vectors and transformed host cells are also provided. The KGA channels exhibit inward rectification and are activated by a G-protein. The products of the invention are useful in screening assays to identify modulators of the KGA channel and in methods for identifying or preparing nucleic acids encoding the KGA channel or related potassium channels.

17 Claims, 9 Drawing Sheets

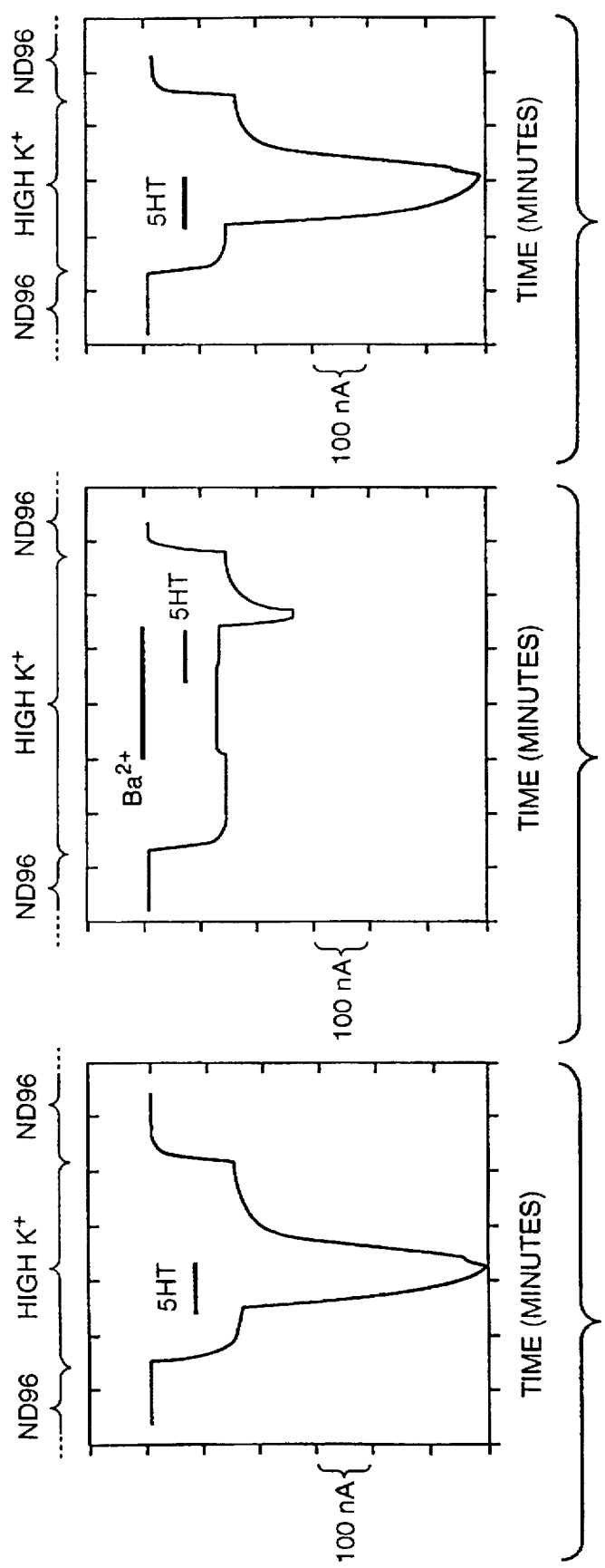

FIGURE 5A

```
  1 GGCA CGA GAA TCT GGA TCT CCC CTC CGT ATT ATG TCT GCA CTC CGA   46
  1                                             M   S   A   L   R   S

47 AGG AAA TTT GGG GAC GAT TAC CAG GTA GTG ACC ACT TCG TCC AGC   91
  6   R   K   F   G   D   D   Y   Q   V   V   T   T   S   S   S   20

92 GGT TCG GGC TTG CAG CCC CAG GGG CCA GGA CAG GGC CCA CAG CAG  136
 21   G   S   G   L   Q   P   Q   G   P   G   Q   G   P   Q   Q   35

137 CAG CTT GTA CCC AAG AAG AAA CGG CAG CGG TTC GTG GAC AAG AAC  181
 36   Q   L   V   P   K   K   K   R   Q   R   F   V   D   K   N   50

182 GGT CGG TGC AAT GTG CAG CAC GGC AAC CTG GGC AGC GAG ACC AGT  226
 51   G   R   C   N   V   Q   H   G   N   L   G   S   E   T   S   65

227 CGC TAC CTT TCC GAC CTC TTC ACT ACC CTG GTG GAT CTC AAG TGG  271
 66   R   Y   L   S   D   L   F   T   T   L   V   D   L   K   W   80

272 CGT TGG AAC CTC TTT ATC TTC ATC CTC ACC TAC ACC GTG GCC TGG  316
 81   R   W   N   L   F   I   F   I   L   T   Y   T   V   A   W   95

317 CTC TTC ATG GCG TCC ATG TGG TGG GTG ATC GCT TAT ACC CGG GGC  361
 96   L   F   M   A   S   M   W   W   V   I   A   Y   T   R   G  110

362 GAC CTG AAC AAA GCC CAT GTC GGC AAC TAC ACT CCC TGT GTG GCC  406
111   D   L   N   K   A   H   V   G   N   Y   T   P   C   V   A  125

407 AAT GTC TAT AAC TTC CCC TCT GCC TTC CTT TTC ATC GAG ACC  451
126   N   V   Y   N   F   P   S   A   F   L   F   F   I   E   T  140

452 GAG GCC ACC ATC GGC TAT GGC TAC CGC TAC ATC ACC GAC AAG TGC  496
141   E   A   T   I   G   Y   G   Y   R   Y   I   T   D   K   C  155

497 CCC GAG GGC ATC ATC CTT TTC CTT TTC CAG TCC ATC CTT GGC TCC  541
156   P   E   G   I   I   L   F   L   F   Q   S   I   L   G   S  170

542 ATC GTG GAC GCT TTC CTC ATC GGC TGC ATG TTC ATC AAG ATG TCC  586
171   I   V   D   A   F   L   I   G   C   M   F   I   K   M   S  185

587 CAG CCC AAA AAG CGC GCC GAG ACC CTC ATG TTT AGC GAG CAT GCG  631
186   Q   P   K   K   R   A   E   T   L   M   F   S   E   H   A  200

632 GTT ATT TCC ATG AGG GAC GGA AAA CTC ACT CTC ATG TTC CGG GTG  676
201   V   I   S   M   R   D   G   K   L   T   L   M   F   R   V  215

677 GGC AAC CTG CGC AAC AGC CAC ATG GTC TCC GCG CAG ATC CGC TGC  721
216   G   N   L   R   N   S   H   M   V   S   A   Q   I   R   C  230

722 AAG CTG CTC AAA TCT CGG CAG ACA CCT GAG GGT GAG TTT CTA CCC  766
231   K   L   L   K   S   R   Q   T   P   E   G   E   F   L   P  245

767 CTT GAC CAA CTT GAA CTG GAT GTA GGT TTT AGT ACA GGG GCA GAT  811
246   L   D   Q   L   E   L   D   V   G   F   S   T   G   A   D  260

812 CAA CTT TTT CTT GTG TCC CCT CTC ACC ATT TGC CAC GTG ATC GAT  856
261   Q   L   F   L   V   S   P   L   T   I   C   H   V   I   D  275

857 GCC AAA AGC CCC TTT TAT GAC CTA TCC CAG CGA AGC ATG CAA ACT  901
276   A   K   S   P   F   Y   D   L   S   Q   R   S   M   Q   T  290
```

FIGURE 5B

```
 902 GAA CAG TTC GAG GTG GTC GTC ATC CTG GAA GGC ATC GTG GAA ACC  946
 291  E   Q   F   E   V   V   V   I   L   E   G   I   V   E   T   305

947 ACA GGG ATG ACT TGT CAA GCT CGA ACA TCA TAC ACC GAA GAT GAA  991
 306  T   G   M   T   C   Q   A   R   T   S   Y   T   E   D   E   320

992 GTT CTT TGG GGT CAT CGT TTT TTC CCT GTA ATT TCT TTA GAA GAA 1036
 321  V   L   W   G   H   R   F   F   P   V   I   S   L   E   E   335

1037 GGA TTC TTT AAA GTC GAT TAC TCC CAG TTC CAT GCA ACC TTT GAA 1081
 336  G   F   F   K   V   D   Y   S   Q   F   H   A   T   F   E   350

1082 GTC CCC ACC CCT CCG TAC AGT GTG AAA GAG CAG GAA GAA ATG CTT 1126
 351  V   P   T   P   P   Y   S   V   K   E   Q   E   E   M   L   365

1127 CTC ATG TCT TCC CCT TTA ATA GCA CCA GCC ATA ACC AAC AGC AAA 1171
 366  L   M   S   S   P   L   I   A   P   A   I   T   N   S   K   380

1172 GAA AGA CAC AAT TCT GTG GAG TGC TTA GAT GGA CTA GAT GAC ATT 1216
 381  E   R   H   N   S   V   E   C   L   D   G   L   D   D   I   395

1217 AGC ACA AAA CTT CCA TCG AAG CTG CAG AAA ATT ACG GGG AGA GAA 1261
 396  S   T   K   L   P   S   K   L   Q   K   I   T   G   R   E   410

1262 GAC TTT CCC AAA AAA CTC CTG AGG ATG AGT TCT ACA ACT TCA GAA 1306
 411  D   F   P   K   K   L   L   R   M   S   S   T   T   S   E   425

1307 AAA GCC TAT AGT TTG GGT GAT TTG CCC ATG AAA CTC CAA CGA ATA 1351
 426  K   A   Y   S   L   G   D   L   P   M   K   L   Q   R   I   440

1352 AGT TCG GTT CCT GGC AAC TCT GAA GAA AAA CTG GTA TCT AAA ACC 1396
 441  S   S   V   P   G   N   S   E   E   K   L   V   S   K   T   455

1397 ACC AAG ATG TTA TCA GAT CCC ATG AGC CAG TCT GTG GCC GAT TTG 1441
 456  T   K   M   L   S   D   P   M   S   Q   S   V   A   D   L   470

1442 CCA CCG AAG CTT CAA AAG ATG GCT GGA GGA CCT ACC AGG ATG GAA 1486
 471  P   P   K   L   Q   K   M   A   G   G   P   T   R   M   E   485

1487 GGG AAT CTT CCA GCC AAA CTA AGA AAA ATG AAC TCT GAC CGC TTC 1531
 486  G   N   L   P   A   K   L   R   K   M   N   S   D   R   F   500

1532 ACA TAG CAA AAC ACC CCA TTA GGC ATT ATT TCA TGT TTT GAT TTA 1576
 501  T   *                                                       515

1577 GTT TTA GTC CAA TAT TTG GCT GAT AAG ATA ATC CTC CCC GGG AAA 1621

1622 TCT GAG AGG TCT ATC CCA GTC TGG CAA ATT CAT CAG AGG ACT CTT 1666

1667 CAT TGA AGT GTT GTT ACT GTG TTG AAC ATG AGT TAC AAA GGG AGG 1711

1712 ACA TCA TAA GAA AGC TAA TAG TTG GCA TGT ATT ATC ACA TCA AGC 1756

1757 ATG CAA TAA TGT GCA AAT TTT GCA TTT AGT TTT CTG GCA TGA TTT 1801

1802 ATA TAT GGC ATA TTT ATA TTG AAT ATT CTG GAA AAA TAT ATA AAT 1846

1847 ATA TAT TTG AAG TGG AGA TAT TCT CCC CAT AAT TTC TAA TAT ATG 1891

1892 TAT TAA GCC AAA CAT GAG TGG ATA GCT TTC AGG GCA CTA AAA TAA 1936

1937 TAT ACA TGC ATA CAT ACA TAC ATG CAT ATG CAC AGA CAC ATA CAC 1981
```

FIGURE 5C

```
1982  ACA CAT ACT CAT ATA TAT AAA ACA TAC CCA TAC AAA CAT ATA TAT    2026
2027  CTA ATA AAA ATT GTG ATG TTT TGT TCA AAA AAA AAA AAA AAA AA     2070
```

DNA ENCODING INWARD RECTIFIER, G-PROTEIN ACTIVATED, MAMMALIAN, POTASSIUM KGA CHANNEL AND USES THEREOF

The invention disclosed herein was made with U.S. Government support under USPHS grants GM29836 and MH49176. Accordingly, the U.S. government has certain rights in this invention.

BACKGROUND OF THE INVENTION

Throughout this application various publications are referenced by their reference number within parentheses. Full citations for these publications may be found at the end of the specification immediately preceding the sequence listing. The disclosures of these publications in their entireties are hereby incorporated by reference into this application in order to more fully describe the state of the art to which this invention pertains.

Parasympathetic regulation of the rate of heart contraction is exerted through the release of acetylcholine (ACh), which opens a $K^+$ channel in the atrium and thus slows the rate of depolarization that leads to initiation of the action potential (1,2). The coupling between binding of ACh to a muscarinic receptor and opening of the $K^+$ channel occurs via a pertussis toxin (PTX)-sensitive heterotrimeric G-protein, $G_k$(3–5), probably belonging to the $G_i$ family (6,7). Activation of this G-protein-activated $K^+$ channel by $G_k$ does not require cytoplasmic intermediates (reviewed in refs. 8,9). However, a long-standing controversy exists as to which G-protein subunit couples to the KG channel. Purified $\beta\gamma$ subunit complex (10,11) and $\alpha$ subunits of $G_i$ family (6,7, 12) activate the KG channel in cell free, inside-out patches of atrial myocytes. Activation by the $\alpha$ subunits occurs at lower concentrations than that by $\beta\gamma$, but seems to be less efficient (13); the relative physiological importance of each pathway, as well as of possible involvement of the arachidonic acid pathway (14), is unclear.

A channel similar or identical to the ACh-operated KG can be activated in the atrium by adenosine (15), ATP (16), and epinephrine (17), probably also via a G-protein pathway. Furthermore, in nerve cells various 7-helix receptors such as serotonin 5HT1A, δ-opioid, $GABA_B$, somatostatin, etc., couple to similar $K^+$ channels, probably through direct activation by G-proteins (18–22). The similarity of the channels and of the signaling pathways in atrium and some nerve cell preparations was strengthened by the demonstration of the coupling of a neuronal 5HT1A receptor (5HT1A-R), transiently expressed in atrial myocytes, to the atrial KG (23).

By electrophysiological and pharmacological criteria, the atrial KGA channel belongs to a family of inward rectifiers that conduct $K^+$ much better in the inward than the outward direction, are blocked by extracellular $Na^+$, $Cs^+$ and $Ba^{2+}$, and are believed to possess a single-file pore with several permeant and blocking ion binding sites (24). Many inward rectifiers are not activated by transmitters or voltage but seem to be constitutively active. Inward rectification of the atrial KGA channel is due to block of $K^+$ efflux by intracellular $Mg^2$ (25), but for some channels of this family inward rectification may not depend on $Mg^{2+}$ block (26,27). The molecular structures of atrial and neuronal KGs are unknown. Inwardly rectifying $K^+$ channels structurally similar to voltage-activated $K^+$ channels have been cloned from plant cells (28,29). Recently, the primary structures of two mammalian inward rectifier channels have been elucidated by molecular cloning of their cDNAs via expression in Xenopus oocytes: an ATP-regulated $K^+$ channel from kidney, ROMK1 (30), and an inward rectifier from a macrophage cell line, IRK1 (31). Both appear to belong to a new superfamily of $K^+$ channels, with only two transmembrane domains per subunit and a pore region homologous to that of $K^+$, $Ca^{2+}$ and $Na^+$ voltage-dependent channels (see ref. 32). It has been hypothesized that the structure of G-protein activated inward rectifying $K^+$ channels should be similar to that of ROMK1 and IRK1 (31). Cloning of the atrial KGA channel and its expression in a heterologous system would be of importance not only for testing this hypothesis, but also because it will allow an as yet unexplored molecular approach to investigation of the mechanisms of direct G-protein-ion channel coupling. As a first step to cloning of the atrial KGA channel we have expressed it in Xenopus oocyte injected with atrial RNA and characterized the macroscopic current properties, including a preliminary characterization of G-protein coupling. We cloned the atrial KGA from a cDNA library derived from mRNA extracted from the heart of a 19 day old rat.

SUMMARY OF THE INVENTION

This invention provides isolated nucleic acid molecules which encode inward rectifier, G-protein activated, mammalian, potassium KGA channel.

This invention also provides a nucleic acid molecule of at least 15 nucleotides capable of specifically hybridizing with the above nucleic acid molecule.

This invention further provides a vector comprising the isolated nucleic acid molecules encoding an inward rectifier, G-protein activated, mammalian, potassium KGA channel.

This invention provides a host vector system for the production of a polypeptide having the biological activity of KGA channel which comprises the above vector in a suitable host.

This invention also provides a method for isolating from a sample a nucleic acid molecule encoding an inward rectifier, G-protein activated, potassium channel in a sample which comprises: (a) isolating the nucleic acids from the sample; (b) contacting the isolated nucleic acids with the molecule of at least 15 nucleotides capable of specifically hybridizing with the above nucleic acid molecule which encode inward rectifier, G-protein activated, mammalian, potassium KGA channel under the conditions permitting complex formation between the nucleic acid molecule encoding an inward rectifier, G-protein activated, potassium channel and the nucleic acid molecule of at least 15 nucleotides capable of specifically hybridizing with the above nucleic acid molecule which encode inward rectifier, G-protein activated, mammalian, potassium KGA channel; (c) isolating the complex formed; and (d) separating the nucleic acid molecule encoding an inward rectifier, G-protein activated, potassium channel from the complex, thereby isolating the nucleic acid molecule encoding an inward rectifier, G-protein activated, potassium channel.

BRIEF DESCRIPTION OF FIGURES

FIG. 1A $I_{hK}$ and $I_{5HT}$ in an oocyte injected with atrial RNA+5HT1A-R RNA. Holding potential in this and all following Figures was −8 mV. FIG. 1B Inward currents evoked by ACh (AcCHo) and 5HT in a single oocyte in hK solution. FIG. 1C The dependence of $I_{5HT}$ amplitude on 5HT concentration in oocytes of one frog. In each oocyte, the response to one 5HT concentration was tested. Data represent mean±SEM in 4–6 cells at each concentration.

FIG. 2A Currents evoked by voltage steps from the holding potential of −80 mV to voltages between −140 and 40 mV in 20 mV steps in ND96(a), hK (b), hK in the presence of 5HT (c). Net $I_{5HT}$ (d) was obtained by digital subtraction of (b) from (c). FIG. 2B Current-voltage relations of the total membrane current in a representative oocyte in NG 96 (2 mM [Kout]; □), in 25 mM [K⁺ out] (♦); in 75 mM [Kout] (○, and in hK (96 mM [Kout]; ▲). FIG. C Current-voltage relation of the net $I_{5HT}$ in the same oocyte as in FIG. 2B in 25 mM [Kout] (♦), 75 mM [Kout] (○), and 96 mM [Kout] (▲). FIG. 2D The dependence of the reversal potentials of total membrane current (▲) and of $I_{5HT}$ (♦) on [Kout]. The straight lines represent least square fits to data (mean±SEM, n=3 for each point).

FIGS. 3A–3D. Ba²⁺ block of $I_{hK}$ and $I_{5HT}$ (FIGS. 3A–3C), records taken from the same oocyte at 10 min intervals. Between the records, the cell was bathed in ND96. 5HT concentration was 4 nM. Note that in FIG. 3B 300 μM Ba²⁺ reduces $I_{hK}$ and almost completely blocks $I_{5HT}$. Ba²⁺ and 5HT were washed out simultaneously, and this resulted in an inward current "tail". FIG. 3D dose dependence of Ba²⁺ inhibition of $I_{hK}$ in native oocytes (○), $I_{hK}$ in RNA-injected oocytes (●), $I_{5HT}$ in RNA-injected oocytes (▽). Data are mean±SEM, n=3 to 7 for each point.

FIG. 4A The effect of PTX treatment (500 ng/ml, 20–26 h) on $I_{hK}$ and $I_{5HT}$. The cells were injected with 120 ng/oocyte total atrial RNA, 11 ng/oocyte 5HT1A-R RNA, and, where indicated, with 11 ng/oocyte $G_{i2}\alpha$ RNA. FIG. 4B GDP-β-S injection inhibits $I_{5HT}$ but not $I_{hK}$ in an oocyte injected with atrial+5HT1A-R RNAs. 5HT concentration was 0.4 μM. A small outward current deflection (denoted by ⋆) upon washout of 5HT was caused by an inadvertent perfusion of ND96 for a few seconds.

FIGS. 5A–5C. Nucleotide and deduced amino acid sequence encoding the inward rectifier, G-protein associated, mammalian, potassium KGA channel (A–C). Numbers in the right hand margin correlate to nucleotide position and numbers below the amino acid sequence correlate with amino acid position.

DETAILED DESCRIPTION OF THE INVENTION

Figure 1A:
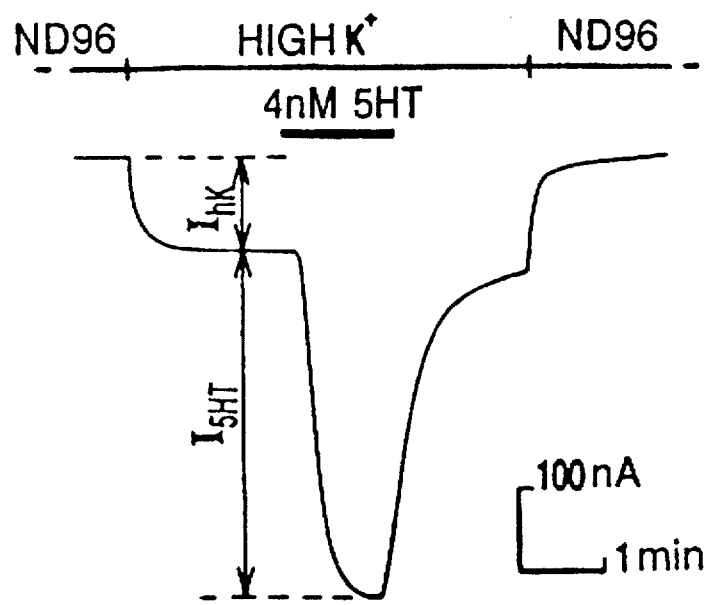
FIGS. 1A–1C. Inward currents evoked by high $K^+$, 5HT and ACh in RNA-injected oocytes.

This invention provides isolated nucleic acid molecules which encode inward rectifier, G-protein activated, mammalian, potassium KGA channel. As used herein, the term inward rectifier, G-protein activated, mammalian, potassium KGA channel encompasses any amino acid sequence, polypeptide or protein having biological activities provided by the inward rectifier, G-protein activated, mammalian, potassium KGA channel. Furthermore the G-protein activation can be either directly or indirectly, and involve one or more G-proteins.

In one embodiment of this invention, the isolated nucleic acid molecules described hereinabove are DNA. In other embodiments of this invention, the isolated nucleic acid molecules described hereinabove are cDNA, genomic DNA or RNA. In the preferred embodiment of this invention, the isolated nucleic acid molecule is a cDNA as shown in sequence ID number 1.

This invention also encompasses DNAs and cDNAs which encode amino acid sequences which differ from those of inward rectifier, G-protein activated, mammalian, potassium KGA channel, but which should not produce functional changes in the KGA channel. This invention also encompasses nucleic acid molecules of at least 15 nucleotides capable of specifically hybridizing with the nucleic acid molecule which encode inward rectifier, G-protein activated, mammalian, potassium KGA channel. Hybridization methods are well known to those of skill in the art.

The DNA molecules of the subject invention also include DNA molecules coding for polypeptide analog, fragments or derivatives of substantially similar polypeptides which differ for naturally-occurring forms in terms of the identity of location of one or more amino acid residues (deletion analogs containing less than all of the residues specified for the protein, substitution analogs wherein one or more residues are replaced by other residues and addition analog wherein one or more amino acid residues is added to a terminal or medial portion of the polypeptides) and which share some or all properties of naturally-occurring forms. These sequences include: the incorporation of codons preferred for expressions by selected non-mammalian host; the provision of sites for cleavage by restriction endonuclease enzymes; the addition of promoters operatively linked to enhance RNA transcription; and the provision of additional initial, terminal or intermediate DNA sequences that facilitate construction of readily expressed vectors.

The nucleic acid molecule described and claimed herein is useful for the information which it provides concerning the amino acid sequence of the polypeptide and as products for the large scale synthesis of the polypeptide by a variety of recombinant techniques. The nucleic acid molecule is useful for generating new cloning and expression vectors, transformed and transfected procaryotic and eucaryotic host cells, and new and useful methods for cultured growth of such host cells capable of expressing the inward rectifier, G-protein activated, mammalian, KGA potassium channel and related polypeptides with biological activity of the KGA channel. Capable hosts for such host vector systems may include but are not limited to a bacterial cell, an insect cell, a mammalian cell, and a Xenopus oocyte.

The isolated RNA molecule described and claimed herein is useful for the information it provides concerning the amino acid sequence of the polypeptide and as a product for synthesis of the polypeptide by injecting the RNA molecules into Xenopus oocytes and culturing the oocytes under conditions that are well known to an ordinary artisan.

Moreover, the isolated nucleic acid molecules are useful for the development of probes to screen for and isolate related molecules from nucleic acid libraries other tissues, or organisms.

Inward rectifier, G-protein activated, mammalian, potassium KGA channel may be produced by a variety of vertebrate animals. In an embodiment, a rat inward rectifier, G-protein activated, mammalian, potassium KGA channel is isolated. A sequence of the DNA of rat inward rectifier, G-protein activated, mammalian, potassium KGA channel is shown in FIG. 5.

The resulting plasmid, pBSIIKS(−)KGA, encoding the rat inward rectifier, G-protein activated, mammalian, potassium KGA channel was deposited on May 17, 1993 with the American Type Culture Collection (ATCC), 12301 Parklawn Drive, Rockville, Md. 20852, U.S.A., under the provisions of the Budapest Treaty for the International Recognition of the Deposition of Microorganism for the Purposes of Patent Procedure. Plasmid, pBSIIKS(−)KGA, was accorded ATCC accession number 75469.

Throughout this application, references to specific nucleotides are to nucleotides present on the coding strand of the nucleic acid. The following standard abbreviations are used throughout he specification to indicate specific nucleotides:

C = cytosine  A = adenosine
T = thymidine  G = guanosine

For the purpose of illustration only, applicants used a CDNA plasmid library derived from 19-day-old rat atrial mRNA. The DNA was synthesized from the mRNA by reverse transcriptase using a poly(dt) primer with a XhoI overhang and was methylated. Adapters with EcoRI sites were ligated to both ends and the CDNA was digested with XhoI. It was ligated into XhoI-EcoRI-digested pBluescriptII KS(–). The library was linearized and amplified by polymerase chain reaction of the cDNA using primers that were complementary to sequences flanking the CDNA insert. cRNA was synthesized in vitro from the T7 promoter using T7 RNA polymerase. The cRNA was microinjected into Xenopus laevis oocytes and electrophysiological recordings under conditions described in Experimental Materials and Methods determined indentification of a inward rectifier, G-protein activated, mammalian, potassium KGA channel. Fewer and fewer CDNA clones from the library were used after identification of the KGA channel until the cDNA of the inward rectifier, G-protein activated, mammalian, potassium KGA channel was isolated.

This invention provides a nucleic acid probe comprising a nucleic acid molecule of at least 15 nucleotides capable of specifically hybridizing with a sequence included within the sequence of a nucleic acid molecule encoding an inward rectifier, G-protein activated, mammalian, potassium KGA channel. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skill in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes inward rectifier, G-protein activated, mammalian potassium KGA channel into suitable vectors, such as plasmids, bacteriophages, or retroviral vectors followed by transforming into suitable host cells and harvesting of the DNA probes, using methods well known in the art. Alternatively, probes may be generated chemically from DNA synthesizers.

The probes are useful for 'in situ' hybridization to locate tissues which express this gene, or for other hybridization assays for the presence of this gene or its in RNA in various biological tissues.

Vectors which comprise the isolated nucleic acid molecule described hereinabove also are provided. Suitable vectors comprise, but are not limited to, a plasmid or a virus. These vectors may be transformed into a suitable host cell to form a host cell vector system for the production of a polypeptide having the biological activity of inward rectifier, G-protein activated, mammalian potassium KGA channel.

This invention further provides an isolated DNA or cDNA molecule described hereinabove wherein the host cell is selected from the group consisting of bacterial cells such as E. coli), yeast cells, fungal cells, insect cells and animal cells. Suitable animal cells include, but are not limited to Cos cells, HeLa cells, L(tk-), and various primary mammalian cells.

This invention provides a method for isolating from a sample a nucleic acid molecule encoding an inward rectifier, G-protein activated, potassium channel using the probe generated from the rat inward rectifier, G-protein activated, mammalian, potassium KGA channel gene. For the human, inward rectifier, G-protein activated, mammalian, potassium KGA channel, it is conceivable that the degree of homology between rat and human could be considerable. Homology studies of the inward rectifier, G-protein activated, mammalian, potassium KGA channel using Genetics Computer Group Sequence Analysis Software, Version 7.2, revealed 55% identity with Human clone HHCMD37 (Genbank Accession # M78731). Human heart cDNA library and human genomic library may be used for such screening. Duplicate filters of human libraries may be screened with radio labelled probe derived from the rat inward rectifier, G-protein activated, mammalian, potassium KGA channel DNA molecule. The filters containing the human libraries will be hybridized with the probe at low stringency (Sambrook, et al 1989) and positive clones identified.

This invention provides a method to identify and purify inward rectifier, G-protein activated, potassium channels. A sample of nucleic acid molecules can be screened for nucleic acid molecules capable of supporting complex formations with an inward rectifier, G-protein activated, mammalian, KGA potassium channels nucleic acid molecule of at least 15 nucleotides under conditions well known in the art that cause complex formation between nucleic acids molecules. "Sample" as used herein includes but is not limited to genomic libraries, cDNA libraries, nucleic acid molecule extracts from tissue, or nucleic acid molecule extracts from cell culture. Conditions that pertain to complex formation between nucleic acids are well understand by an ordinary skilled artisan and include but are not limited to suboptimal temperature, ionic concentration, and size of the nucleic acid molecule. After complex formation between the nucleic acid molecule encoding the inward rectifier, G-protein activated, mammalian, KGA potassium channel and another nucleic acid, the other nucleic acid molecule can be isolated by methods known in the art.

This invention provides a method for isolating from a sample a nucleic acid molecule encoding an inward rectifier, G-protein activated, potassium channel in a sample which comprises: (a)isolating the nucleic acids from the sample; (b) contacting the isolated nucleic acids with the nucleic acid molecule of at least 15 nucleotides capable of specifically hybridizing with the nucleic acid molecule of an isolated nucleic acid molecule encoding an inward rectifier, G-protein activated, mammalian, potassium KGA channel under the conditions permitting complex formation between the nucleic acid molecule encoding an inward rectifier, G-protein activated, potassium channel and the nucleic acid molecule of at least 15 nucleotides capable of specifically hybridizing with the nucleic acid molecule of an isolated nucleic acid molecule encoding an inward rectifier, G-protein activated, mammalian, potassium KGA channel; (c) isolating the complex formed; and (d) separating the nucleic acid molecule encoding an inward rectifier, G-protein activated, potassium channel from the complex, thereby isolating the nucleic acid molecule encoding an inward rectifier, G-protein activated, potassium channel.

This invention further provides a method for isolating DNA encoding an inward rectifier, G-protein activated, potassium channel or a fragment thereof in a sample which comprises: (a) isolating the DNA from the sample; (b) denaturing the isolated DNA; (c) reannealing the denatured nucleic acids in the presence of two unique single stranded nucleic acid molecules of at least 15 nucleotides capable of specifically hybridizing with the nucleic acid molecule of the inward rectifier, G-protein associated, mammalian, potassium KGA channel that are complementary to nucleotide sequences on opposite strands of an isolated DNA molecule encoding an inward rectifier, G-protein activated, mammalian, potassium KGA channel; (d) polymerizing the reannealed nucleic acids with DNA polymerase under conditions that allow DNA polymerization; (e) denaturing the polymerized DNA in (d); (f) repeating steps (c) through (e) for more than 10 cycles; and (g) isolating the polymerization product in step (f). The term "unique" as used herein defines a nucleic acid molecule that does not contain known genomic repeated sequences, including but not limited to Alu sequences.

This invention provides a method for isolating DNA encoding an inward rectifier, G-protein activated, potassium channel or a fragment thereof in a sample which comprises: (a) isolating the DNA from the sample; (b) denaturing the isolated DNA; (c) reannealing the denatured nucleic acids in the presence of a unique single stranded nucleic acid molecules of at least 15 nucleotides capable of specifically hybridizing with the nucleic acid molecule of the inward rectifier, G-protein associated, mammalian, potassium KGA channel that is complementary to nucleotide sequences of an isolated DNA molecule encoding an inward rectifier, G-protein activated, mammalian, potassium KGA channel and a single stranded nucleic acid molecule encoding a known genomic repeat sequence; (d) polymerizing the reannealed nucleic acids with DNA polymerase under conditions that allow DNA polymerization; (e) denaturing the polymerized DNA in (d); (f) repeating steps (c) through (e) for more than 10 cycles; and (g) isolating the polymerization product in step (f).

This invention provides the above method for isolating from a sample a nucleic acid molecule encoding an inward rectifier, G-protein activated, potassium channel in a sample wherein, the nucleic acid molecule of at least 15 nucleotides capable of specifically hybridizing with the nucleic acid molecule of an isolated nucleic acid molecule encoding an inward rectifier, G-protein activated, mammalian, potassium KGA channel is labelled with a detectable marker.

The invention provides the nucleic acid molecule isolated by the above method for isolating from a sample a nucleic acid molecule encoding an inward rectifier, G-protein activated, potassium channel in a sample.

This invention provides a purified inward rectifier, G-protein activated, mammalian, potassium KGA channel.

This invention also provides the above-described purified channel having substantially the same amino acid sequence as the amino acid sequence shown in FIGS. 5A–5C.

This invention provides a protein encoded by the above-described isolated nucleic acid molecule.

This invention provides a method for determining whether an agent activates a KGA channel which comprises: (a) contacting the host vector system of claim 10 with the agent under conditions permitting the KGA channel conductance to be affected by known ion channel agonists or intracellular second messenger agonists; and (b) detecting any change in KGA channel conductance, an increase in KGA channel conductance indicating that the agent activates the KGA channel. The term "agent" as used herein describes any molecule, protein, or pharmaceutical with the capability of directly or indirectly altering ion channel conductance by affecting second messenger systems or the ion channel directly. Agents include but are not limited to serotonin, neurotropin, enkephalins, dopamine, arachidonic acid, cholera toxin, and pertussis toxin. The term "activators" as used herein defines any agent which activates a G-protein associated receptor. The term "activates" as used herein is applied to both G-protein associated receptors and ion channel conductance and in terms of G-protein associated receptors defines the state of the receptor wherein it initiates release of a G-protein subunit which in turn initiates a cellular response. In terms of the ion channel conductance "activates" defines the state of the channel wherein the channel increases conductance. The term "deactivates" as used herein defines the state of the channel wherein the channel is initiated to decrease conductance or is incapable of conductance under conditions when the channel normally conducts ions across a membrane.

This invention also provides the agent identified by the above method.

This invention provide a pharmaceutical composition comprising an amount of the above agent effective to increase KGA conductance and a pharmaceutical acceptable carrier.

This invention provides a method for determining whether an agent deactivates KGA channel conductance which comprises: (a) contacting the host vector system for the production of a polypeptide having the biological activity of KGA channel which comprises the vector comprising the nucleic acid molecule encoding an inward rectifier, G-protein activated, mammalian, potassium KGA channel operatively linked to a promoter of RNA transcription in a suitable host with the agent under conditions permitting the KGA channel conductance to be affected by known ion channel antagonists or intracellular second messenger system agonist; and (b) detecting any change in KGA channel conductance, a decrease in KGA channel conductance indicating that the agent deactivates the KGA channel. The term "agonist" as used herein defines an agent that initiates activation of ion channel conductance or initiates activation of a second messenger system. The term "antagonist" as used herein defines an agent initiates deactivation of ion channel conductance or initiates deactivation of a second messenger system.

This invention provides agents identified by the above method for determining whether an agent deactivates KGA channel conductance.

This invention provides a pharmaceutical composition comprising an amount of the above agent effective to decrease KGA channel conductance and a pharmaceutical acceptable carrier.

This invention provides a method for identifying in a nucleic acid sample a nucleic acid molecule encoding a G-protein associated receptor which activates the inward rectifier, G-protein activated, mammalian, KGA potassium channel which comprises: (a)introducing nucleic acid molecules of claim 1 and sample to a Xenopus oocyte under conditions permitting expression of both the receptor and the channel;(b) contacting the oocyte of step (a) with a panel of known G-protein associated receptor activators; and (c) detecting any change in KGA channel conductance, an increase in KGA channel conductance indicating the identification of a G-protein associated receptor which activates the KGA channel.

This invention provides a method for isolating from a CDNA expression library a G-protein associated receptor which activates the inward rectifier, G-protein activated, mammalian potassium KGA channel which comprises: (a)

isolating cDNA from a sample containing a number of clones of the cDNA expression library;(b) linearizing cDNA sample if necessary;(c) transcribing the linearized cDNA; (d) isolating the RNA from the transcribed cDNA; (e) introducing the isolated RNA and nucleic acid molecules of claim 1 into a Xenopus oocyte under conditions permitting expression of the KGA channel and G-protein associated receptor; (f) contacting the oocyte of step (e) with a panel of known G-protein associated receptor activators; (g) detecting change in KGA channel conductance; and (h) repeating steps (a) through (g) when an increase in KGA channel conductance is detected in step (g) using fewer cDNA clones from the sample until isolation of a single cDNA clone encoding a G-protein associated receptor which activates the KGA channel.

The invention provides a cDNA encoding the G-protein associated receptor isolated in the above method for isolating from a cDNA expression library a G-protein associated receptor which activates the inward rectifier, G-protein activated, mammalian potassium KGA channel.

The invention provides a G-protein associated receptor isolated in the above method for isolating from a cDNA expression library a G-protein associated receptor which activates the inward rectifier, G-protein activated, mammalian potassium KGA channel.

This invention provides a method for testing whether a G-protein associated receptor activates the inward rectifier, G-protein activated, mammalian, KGA potassium channel which comprises: (a) introducing a nucleic acid molecule of claim 1 and a nucleic acid molecule encoding the G-protein associated receptor to a Xenopus oocyte under conditions permitting expression of both the receptor and the channel; (b) contacting the oocyte of step (a) with a known G-protein associated receptor activator; and (c) detecting any change in KGA channel conductance, an increase in KGA channel conductance indicating that the G-protein associated receptor activates the KGA channel.

This invention provides a method for identifying in a nucleic acid sample a G-protein associated receptor capable of deactivating the inward rectifier, G-protein activated, mammalian KGA potassium channel comprising: (a) introducing nucleic acid molecule of claim 1, nucleic acid molecule of a G-protein associated receptor known to activate the KGA channel, and sample of isolated nucleic acids to a Xenopus oocyte under conditions permitting expression of the G-protein associated receptor that activates the KGA channel, the KGA channel and a known G-protein associated receptor; (b) contacting the oocyte of step (a) with a known G-protein associated receptor activator and a panel of known G-protein associated receptor activators; and (c) detecting any change in KGA channel conductance, a decrease in KGA channel conductance indicating the identification of an G-protein associated receptor capable of deactivating the KGA channel in the sample.

This invention provides a method for isolating from a cDNA expression library an G-protein associated receptor which deactivates the inward rectifier, G-protein activated, mammalian potassium KGA channel which comprises: (a) isolating cDNA from a sample containing a number of clones of the cDNA expression library; (b) linearizing cDNA sample if necessary; (c) transcribing the linearized cDNA; (d) isolating the RNA from the transcribed cDNA; (e) introducing the isolated RNA, nucleic acid molecule encoding a known G-protein associated receptor which activates the KGA channel, and nucleic acid molecules of claim 1 into a Xenopus oocyte under conditions permitting expression of the KGA channel and both receptors; (f) contacting the oocyte of step (e) with a known G-protein associated receptor activator and a panel of known inhibitory G-protein associated activators; (g)detecting any change in KGA channel conductance.; and (h) repeating steps (a) through (g) when a decrease in KGA channel conductance is detected in step (g) using fewer number of cDNA clones from the sample until isolation of a single cDNA clone encoding an inhibitory G-protein associated receptor which deactivates the KGA channel.

The invention provides a cDNA encoding the G-protein associated receptor isolated by the above method for isolating from a cDNA expression library a G-protein associated receptor which deactivates the inward rectifier, G-protein activated, mammalian potassium KGA channel.

The invention provides a G-protein associated receptor capable of deactivating the inward rectifier, G-protein activated, mammalian potassium KGA channel isolated by the above method for isolating from a cDNA expression library a G-protein associated receptor which deactivates the inward rectifier, G-protein activated, mammalian potassium KGA channel.

This invention provides a method for identifying an inhibitory G-protein associated receptor which deactivates the inward rectifier, G-protein activated, mammalian KGA potassium channel comprising:(a) introducing the nucleic acid molecule encoding an inward rectifier, G-protein activated, mammalian, potassium KGA channel, a G-protein associated receptor known to activate the KGA channel, and nucleic acid molecules encoding an inhibitory G-protein associated receptor to a Xenopus oocyte under conditions permitting expression of both the receptors and the channel; (b) contacting the oocyte of step (b) with a known G-protein associated receptor activator and a known inhibitory G-protein associated receptor activator; and (c) detecting any change in KGA channel conductance, a decrease in KGA channel conductance indicating that the G-protein associated receptor deactivates the KGA channel.

This invention provides an antibody directed against the purified inward rectifier, G-protein activated, mammalian, potassium KGA channel. In an embodiment, this antibody is monoclonal antibody.

This invention will be better understood from the Experimental Details which follow. However, one skilled in the art will readily appreciate that the specific methods and results discussed are merely illustrative of the invention as described more fully in the claims which follow thereafter.

EXPERIMENTAL MATERIALS AND METHODS

Preparation of RNA and oocytes. Total RNA was extracted from atria and ventricles of 19–21 day old rats of both sexes using the Chomczinski-Sacchi procedure (33). Poly (A) RNA was separated on an oligo-dT cellulose column (type 3, Collaborative Biochemical Products). Ventricle poly(A) RNA was fractionated by centrifugation (18 h, 30,000 g, 4° C.) on a linear 5%–25% sucrose gradient. Xenopus laevis oocytes were prepared as described (34) and injected with either 50–120 ng/oocyte poly(A) RNA, 120–200 ng/oocyte total RNA, or 35 ng/oocyte fractionated poly(A) RNA. In most cases, 5HT1A-R RNA (5–20 ng/oocyte) was co-injected with atrial or ventricle RNA. Final volume of the injected RNA solution was 50 nl. The oocytes were incubated for 3–7 days in the NDE solution (ND96 (see below) containing 1.8 Mm $CaCl_2$ and supplemented with 2.5 Mm Na-pyruvate and 50 µg/ml gentamicin). Occasionally, either 2.5–5% heat-inactivated horse serum or 0.5 mM theophylline were added to the NDE solution. Incubation of oocytes in pertussis toxin (PTX; List Biochemicals) was done in NDE solution without the addition of pyruvate, serum or theophylline. cDNAs of 5HT1A receptor (see 23) and $G_{i2}\alpha$ (a gift from M. I. Simon, Caltech) in pBluescript were linearized, and RNA was synthesized in vitro as described (34).

Electrophysiological recordings were performed using the two electrode voltage clamp method with the Dagan 8500 amplifier (Dagan Instruments, Minneapolis) as described (35). The oocytes were usually kept in the ND96 solution: 96 mM NaCl/2 mM KCl/1 mM $MgCl_2$/1 mM $CaCl_2$/5 mM Hepes, pH=7.5. Most measurements were done in the high $K^+$ solution (hK): 96 mM KCl/2 mM NaCl/1 mM $MgCl_2$/1 mM $CaCl_2$/5 mM Hepes, pH=7.5. Solutions containing intermediate concentrations of $K^+$ were made by substituting $K^+$ for $Na^+$. Solution exchange and drug application were done by superfusing the cell placed in a 0.5 ml chamber. GDP-β-S(trilithium salt; Sigma) was injected by pressure (35). Stimulation, data acquisition, and analysis were performed using pCLAMP software(Axon Instruments, Foster City, Calif.).

EXPERIMENTAL RESULTS

To express the KG channel, the oocytes were injected with atrial total or poly(A) RNA. In order to avoid the possibility that a low level of expression of the muscarinic receptor will make undetectable even a well-expressed KG channel, atrial RNA was usually supplemented with MRNA coding for the serotonin-5HT1A receptor (5HT1A-R); oocytes injected with this RNA mixture will be termed RNA-injected oocytes throughout the paper. When expressed in atrial myocytes, the 5HT1A-R efficiently coupled to the KG channel normally existing in these cells (23), and it was expected to do so in the oocytes.

Four to 5 days after RNA injection addition of 10 μM ACh or 1–2 μM 5HT to the ND96 bath solution did not cause any significant change in membrane current. Therefore, the effects of ACh and 5HT were tested in a high potassium (hK) solution with 96 mM $K^+$ and 2 mM $Na^+$. In this solution, the $K^+$ equilibrium potential ($E_K$) is close to 0 mV, and this enables inward $K^+$ current flow through inwardly rectifying K channels at negative holding potentials (−80 mV was routinely used in this study).

Changing ND 96 to the hK solution was accompanied by the development of an inward current that reached a steady level within 0.5–1 min ($I_{hK}$; FIG. 1A). $I_{hK}$ was also observed in native (not injected with any RNA) oocytes, or in oocytes injected with 5HT1A-R RNA alone, but it was always larger in RNA-injected oocytes (P<0.001, two-tailed t-test; Table 1).

Table 1

Inward currents evoked by high $K^+$ and by 5HT. The entries are inward currents in nA shown as mean±SEM (n), measured at −80 mV in the hK solution. 5HT concentration ranged in different experiments from 100 nM to 2 μM.

| Injected RNA | $I_{hK}$ | $I_{5HT}$ |
| --- | --- | --- |
| None (native oocytes) | 72 ± 6 (34) | 0 (18) |
| 5HT1A-R | 54 ± 4 (11) | 0 (12) |
| Atrial + 5HT1A-R | 123 ± 8 (55) | 290 ± 43 (55) |

Figure 1B:
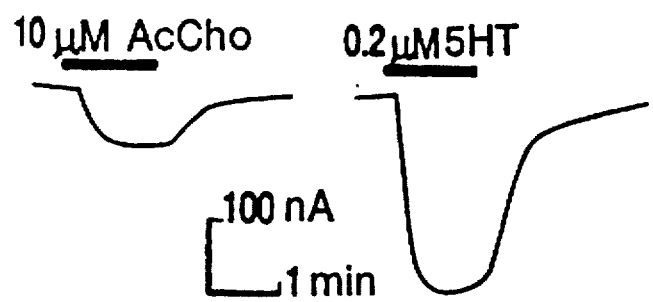

In RNA-injected oocytes, application of 5HT or ACh in hK solution induced an inward current ($I_{5HT}$) that subsided upon washout of the transmitter (FIG. 1A, 1B). The response to ACh was usually smaller than to 5HT when measured in the oocytes of the same frog (FIG. 1B). Thus, in oocytes of one frog $I_{5HT}$ was 1102±84 nA (n=6), whereas the ACh response was 382±45 nA(n=6). $I_{5HT}$ tended to decrease on repeated applications of 5HT, and this could be overcome by increasing the intervals between applications to 10 min or more, suggesting the presence of a desensitization process. $I_{5HT}$ and an increased (in comparison with native oocytes) $I_{hK}$ were also observed in oocytes injected with ventricle poly (A) RNA+5HT1A-R RNA, but the $I_{5HT}$ was about 20 times smaller than with atrial poly(A) RNA (not shown). 5HT had no effect in oocytes injected with atrial RNA without the 5HT1A-R RNA (n=4) or with 5HT1A-R RNA alone, or in native oocytes (Table 1).

Figure 1C:
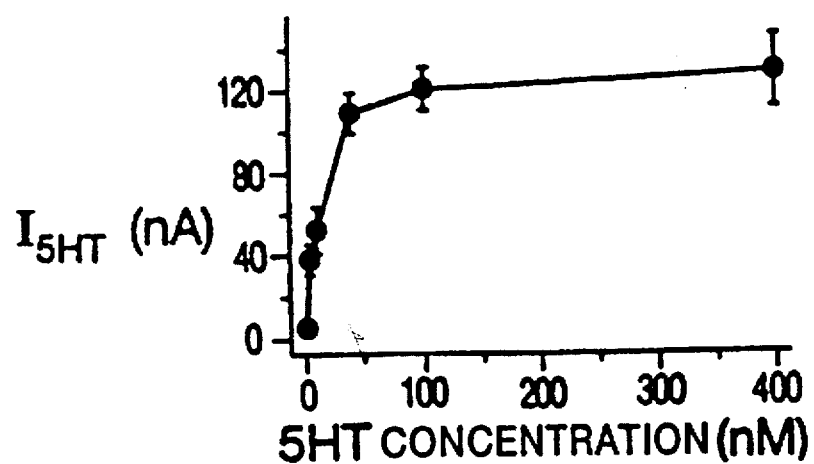

The 5HT dose-response curve showed saturation at about 100 nM and a half-maximal response at about 15 nM (FIG. 1C), which is characteristic of the 5HT1 receptor class (36). A similar current was evoked by a selective 5HT1A agonist, 8-OH DPAT (8-OH-2(D1-n-(propylamino)-tetralin; data not shown).

Figure 2A:
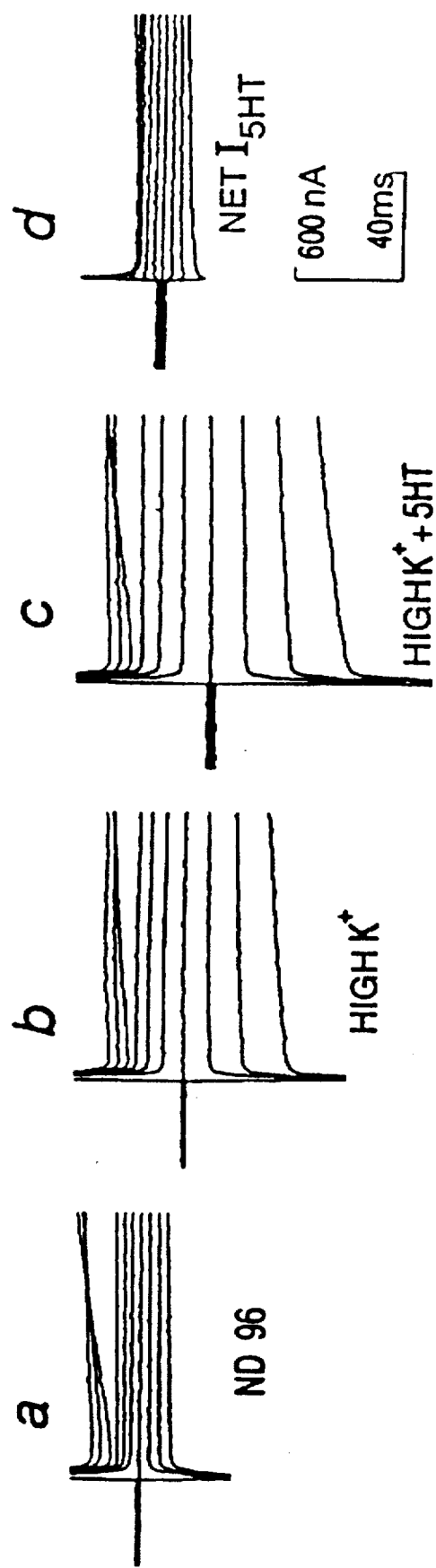
FIGS. 2A–2D. $I_{hK}$ and $I_{5HT}$ are inwardly rectifying K⁺ currents.
Figure 2B:
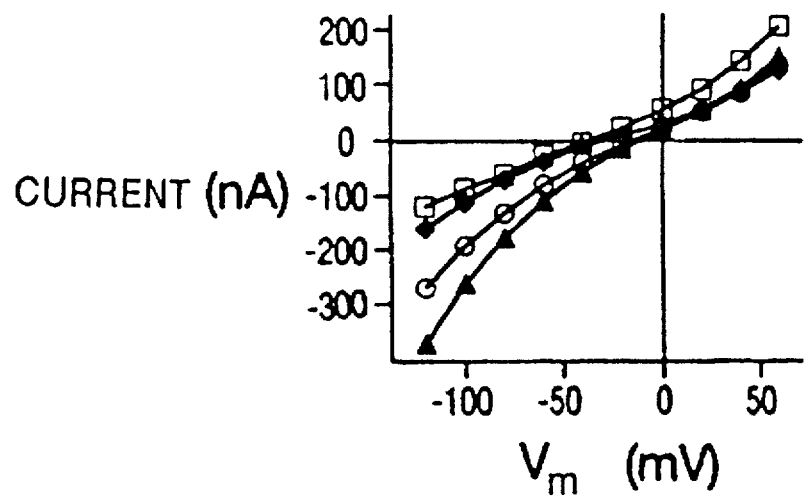
Figure 2C:
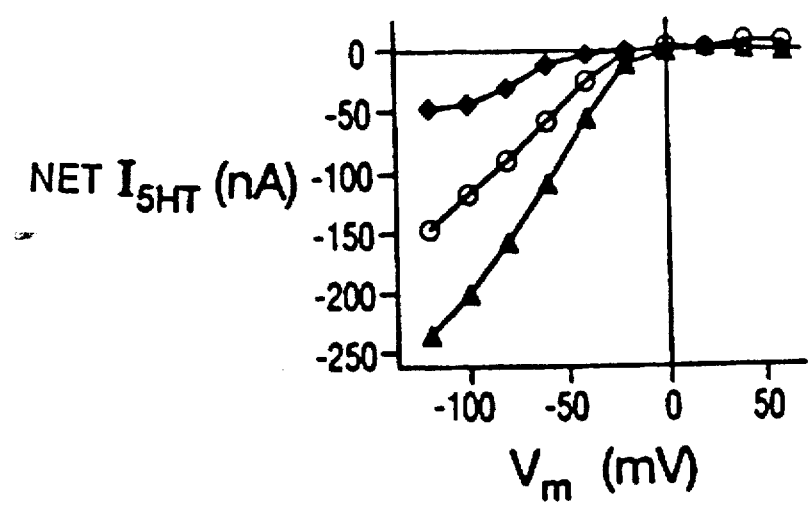
Figure 2D:
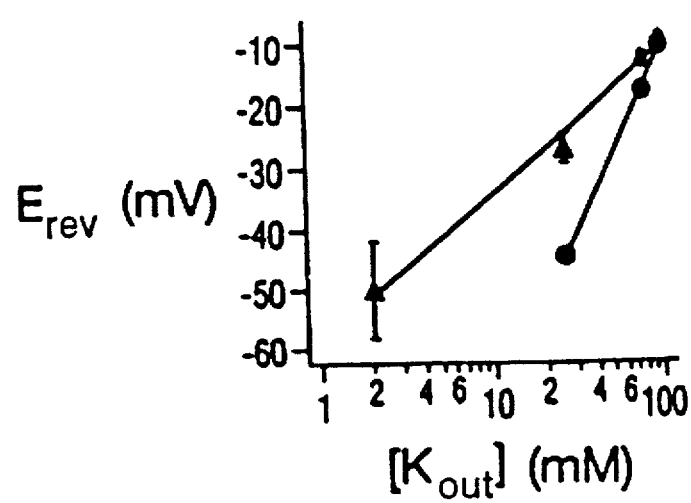

The current-voltage (I-V) characteristic of the oocyte membrane was studied by applying voltage steps from a holding potential of −80 mV. In normal ND96, in the range −140 — −20 mV, only voltage- and time-independent "leak" currents were observed (FIG. 2A), and the I-V curve was linear (FIG. 2B). Above −20 mV, a slowly developing outward current was observed (FIG. 2A, a–c); this is known to be due to opening of a $Cl^-$ channel activated by $Ca^{2+}$ entry through voltage-dependent $Ca^{2+}$ channels (37). The $Ca^{2+}$-activated $Cl^-$ current was also seen in the hK solution; in addition, the total membrane current evoked by steps to −120 and up to −20 mV was larger than in ND96 (FIG. 2Ab; 2B), whereas above 0 mV there was little or no change. This suggested that most or all of $I_{hK}$ elicited at −80 mV by the exchange of ND96 to hK solution was due to a $K^+$ current flowing through a constitutively active inward rectifier $K^+$ channel(s). This current showed some time-dependent inactivation at −140 mV (FIG. 2Ab) and at more negative potentials (not shown); this inactivation phenomenon was not studied further. In the presence of 5HT, the membrane currents between −140 and −20 mV were further increased (FIG. 2Ac). Net 5HT-evoked currents, obtained by digital subtraction of total membrane currents in the absence of 5HT from currents in its presence (FIG. 2Ad), showed clear inward rectification; the 5HT-activated channels conducted little or no current above $E_K$ at different external $K^+$ concentrations, [$K_{out}$] (FIG. 2C). The extrapolated reversal potential of $I_{5HT}$ showed an almost perfect selectivity of the 5HT-activated channel to $K^+$, changing by about 58 mV per 10-fold change in [$K_{out}$] (FIG. 2D). The reversal potential of the total membrane current in the absence of 5HT also depended on [$K_{out}$] (FIG. 2B) but changed only by 24 mV per tenfold change in [$K_{out}$] (FIG. 2D). This does not necessarily imply poor ion selectivity of the constitutively active inward rectifier, but may reflect the relatively high contribution of $Cl^-$ and $Na^+$ to the resting membrane conductance (38).

Figure 3D:
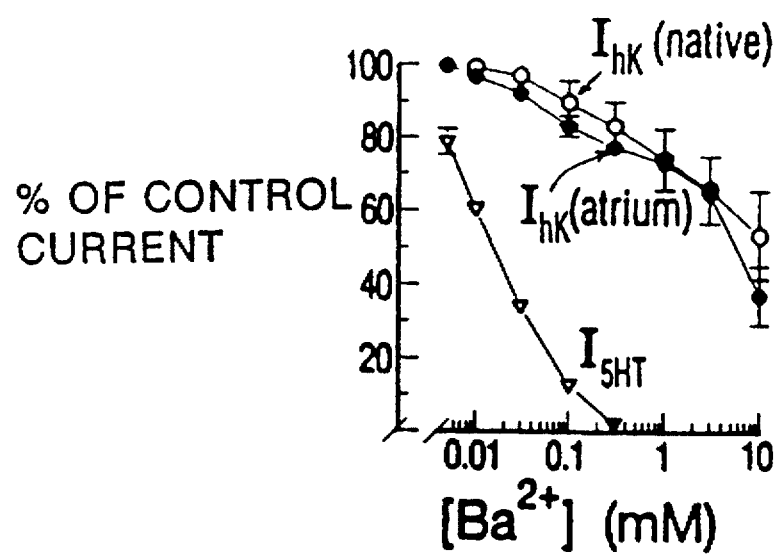

Block by external $Ba^{2+}$ is one of the characteristic features of inward rectifiers (24). In normal ND96 solution, $Ba^{2+}$ (5 μM-3 mM) did not cause any significant changes in resting current or conductance in native or RNA-injected oocytes at the holding potential of −8 mV. In the hK solution, $Ba^{2+}$ inhibited both $I_{hK}$ and $I_{5HT}$ (FIG. 3A–D), and this was accompanied by a decrease in membrane conductance (not shown). 300 μM. $Ba^{2+}$ blocked about 20% of $I_{hK}$ but almost completely abolished $I_{5HT}$ (FIG. 3B). The $IC_{50}$ (halfinhibition concentration) for $Ba^{2+}$ block of $I_{5HT}$ was about 15 μM, whereas $IC_{50}$ for $I_{hK}$ block was above 3 mM (FIG. 3D). It is noteworthy that, although the sensitivity of $I_{hK}$ to $Ba^{2+}$ block was similar in native and RNA-injected oocytes, the latter did appear to have a small component of $I_{hK}$ inhibited by low doses of $Ba^{2+}$ (FIG. 3D). This raises the possibility that the atrial $I_{hK}$ is more sensitive to $Ba^{2+}$ block than the oocyte's $I_{hK}$, or that a fraction of the highly $Ba^{2+}$-sensitive channels underlying $I_{5HT}$ could be active in the absence of agonist. Note also that there was an inward current "tail" observed when $Ba^{2+}$ and 5HT was washed out simultaneously (FIG. 3B), presumably because the rate-limiting step in deactivation of the channel proceeds more slowly than unblock from $Ba^{2+}$.

To estimate the size of RNA encoding the expressed inward rectifiers, ventricle poly(A) RNA (available in large amounts) was fractionated on a sucrose gradient. The size distribution of the fractions was measured by RNA gel blots probed with [$^{32}$P]-labeled poly(T) (39). The RNA encoding $I_{5HT}$ was found mainly in two size fractions covering the range between 2.5 and 5.5 kb. The peak expression of ventricle $I_{hK}$ was in lower size fractions, in the 1.5–3 kb range (data not shown)

Figure 4A:
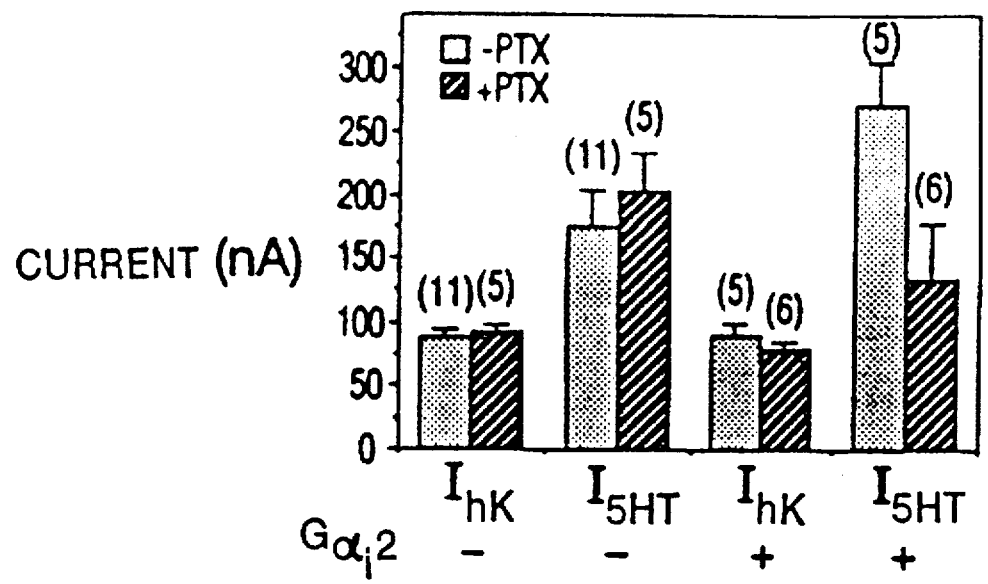
FIGS. 4A–4B. $I_{5HT}$ is mediated by activation of a G-protein.
Figure 4B:
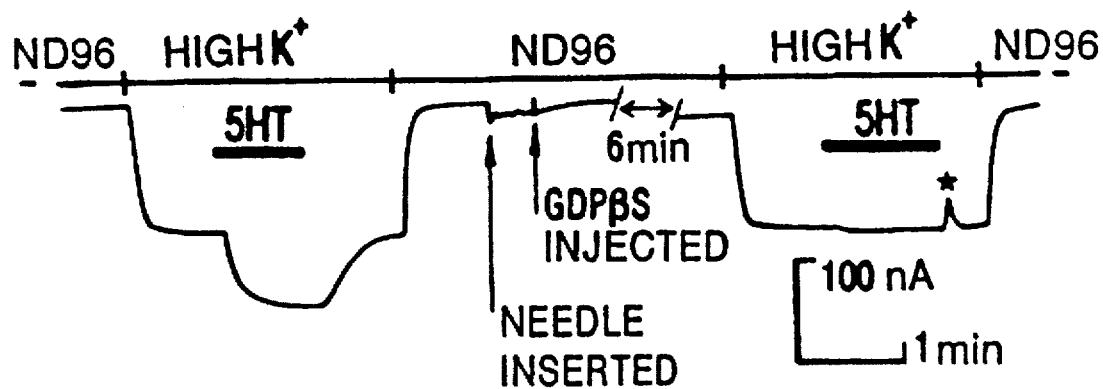

In atrium, the muscarinic receptor is coupled to the KG channel via a PTX-sensitive G-protein (8). Surprisingly, in RNA-injected oocytes, $I_{5HT}$ was not affected by treatment with PTX; neither was $I_{hK}$ (FIG. 4A). To test whether the 5HT1A receptor couples to the $K^+$ channel via a G-protein, the oocytes were injected with 400–800 pmole/oocyte of the non-hydrolysable analog of GDP, GDP-β-S, that is known to inhibit the activity of PTX-sensitive as well as of PTX-insensitive G-proteins (40). In 4 cells, GDP-β-S injection had no effect on $I_{hK}$ (115±8% of control) but strongly inhibited $I_{5HT}$ to 4±1% of control (FIG. 4B). Thus, it appears that the coupling between the 5HT1A receptor and the KG channel occurs via an oocyte's endogenous PTX-insensitive G-protein.

We examined whether an overexpressed PTX-sensitive α subunit of a G-protein, e.g. $G_{i2}α$, could compete with the "native" PTX-insensitive α subunit for the expressed 5HT1A receptor, thus restoring the PTX sensitivity of the KG channel activation. As shown in FIG. 4A, in oocytes injected with atrial RNA plus cRNAs encoding 5HT1A-R and $G_{i2}α$, PTX inhibited $I_{5HT}$ by about 50% (P<0.01, two-tailed t-test), whereas $I_{hK}$ was unaffected.

EXPERIMENTAL DISCUSSION

The present results demonstrate for the first time that the atrial inward rectifier $K^+$ (KG) channel, which in the native tissue is activated by ACh via a PTX-sensitive G-protein, is expressed in oocytes injected with atrial RNA. Current through the channel can be activated by acetylcholine (ACh) or, if RNA encoding a neuronal 5HT1A receptor in co-injected with atrial RNA, by serotonin (5HT). Activation of the channel probably occurs via a muscarinic ACh receptor synthesized following atrial RNA injection, rather than via the oocyte's endogenous muscarinic receptor. The latter couples to phospholipase C, and its activation induces very characteristic large transient Cl⁻ current responses caused by $Ca^{2+}$ release from intracellular stores (41). Fortunately, the majority of oocyte batches lose this response after defolliculation (42), and this response was not observed in the present study. Because the ACh-evoked currents were small in most cases, we concentrated on the study of the 5HT response; the latter was undoubtedly mediated by the introduced 5HT1A receptor, as 5HT was ineffective in oocytes not injected with 5HT1A-RNA, and the response displayed the expected pharmacological properties.

The evidence presented here indicates that, in oocytes injected with atrial and 5HT1A-R RNAs, activation of the 5HT1A receptor leads to opening of a $K^+$ channel that bears distinctive features of an anomalous rectifier, similar to those of the atrial KG: i) it conducts inward but not outward $K^+$ current; ii) it is blocked by low concentrations of $Ba^{2+}$, iii) the conductance of the channel does not depend solely on voltage but on ($E-E_K$). The expression of this channel must truly be directed by atrial RNA, because: i) no hormone or transmitter-activated current of this kind is observed in native oocytes; ii) expression of 5HT1A receptor alone does not cause the appearance of such a response. Based on ventricle RNA fractionation data, the RNA encoding the 5HT-activated channel is in a broad size range between 2.5 and 5.5 kb. This is similar or somewhat smaller than the reported 4–5 kb mRNA size of some constitutively active inward rectifiers expressed in Xenopus oocytes (43, 44), as well as of the cloned IRK1 (5.5 kb; ref. 31) and ROMK1 (4 kb; ref. 30) channels. The properties of $I_{5HT}$ directed by ventricle and atrial RNA are very similar, and it is reasonable to assume that they are encoded by the same RNA species.

Opening of the inward rectifier by 5HT is mediated by activation of a G-protein, as expected for the KG channel, because i) 5HT1A receptor belongs to the family of 7-helix receptors all of which act via G-proteins (40); ii) $I_{5HT}$ was inhibited by intracellular injection of GDP-β-S. However, the G-protein participating in this pathway was PTX-insensitive, possibly an endogenous oocyte G-protein. It is not clear why in the oocyte the channel activation pathway involves a PTX-insensitive G-protein. The atrial KG channel normally couples to $G_i$ (9), and there are at least two subspecies of $G_i$ in the oocyte (45); also, some $G_i$ may be expressed from atrial RNA. Also, in the hippocampus, the 5HT1A receptor opens a $K^+$ channel by activating a PTX-sensitive G-protein (21), one possibility is that a vast excess of this undefined PTX-insensitive G-protein overrides the others in competition for coupling to the 5HT1A receptor. Whatever the reason for this unexpected coupling, our results show that the PTX sensitivity of the KG channel activation can be partially restored by overexpression of the α subunit of $G_i$. Since the actual identify of the α subunit does not seem to be important for activation of the expressed KG channel, these results imply that the βγ subunit complex doublet may be the activator of the channel in this case (cf. 10, 11).

Atrial and ventricle RNAs also induce an enhanced activity of an additional inward rectifier, that is active in the absence of any specific stimulation (referred to as $I_{hK}$ in this paper). $I_{hK}$ in atrial RNA-injected oocytes is about twice as large as in native oocytes or oocytes injected with 5HT1A-R RNA alone. This current does not appear to represent the "basal" activity of the same channel activated by 5HT or ACh because it has a much lower sensitivity to $Ba^{2+}$ block. Moreover, the fractionation data indicates that the RNA directing the expression of $I_{hK}$ is smaller than that encoding the KG channel. However, it is not clear whether this atrial (or ventricle) RNA encodes the channel itself or a factor that enhances the expression or the activity of a native channel. Further studies, such as expression cloning, will help to identify the messages encoding the two inward rectifiers whose expression is reported here.

References

1. Sakmann, B., Noma, A. & Trautwein, W. (1983) Nature 303:250–253.

2. Ijima, T., Irisawa, H. & Kameyama, M. (1985) J. Physiol. (London) 359:485–501.
3. Pfaffinger, P. G., Martin, J. M., Hunter, D. D., Nathanson, N. M. & Hille, B. (1985) Nature 317:536–538.
4. Breitweiser, G. E. & Szabo, G. (1985) Nature 317:538–540.
5. Kurachi, Y., Nakajima, T. & Sugimoto, T. (1986) Am. J. Physiol. 251:H681–H684.
6. Yatani, A., Codina, J., Brown, A. M. & Birnbaumer, L. (1987) Science 235:207–211.
7. Yatani, A., Mattera, R., Codina, J., Graf, R., Okane, K., Pardell, E., Iyengar, R., Brown, A. M. & Birnbaumer, L. (1988) Nature 336:680–682.
8. Kurachi, Y., Tung, R. T., Ito, H. & Nakajima, T. (1992) Prog. Neurobiol. 39:229–246.
9. Brown, A. M. & Birnbaumer, L. (1990) A. Rev. Physiol. 52:197–213.
10. Logothetis, D. E., Kurachi, Y., Galper, J., Neer, E. J. & Clapham, D. E. (1987) Nature 325:321–326.
11. Kurachi, Y., Ito, H., Sugimoto, T., Katada, T. & Ui, M. (1989) Pflugers Arch. 413:325–327.
12. Codina, J., Yatani, A., Grenet, D., Brown, A. M. & Birnbaumer, L. (1987) Sicence 236–442–445.
13. Ito, H., Tung, T. T., Sugimoto, T., Kobayashi, I., Takahashi, K., Katada, T., Ui, M. & Kurachi, Y. (1992) J. Gen. Physiol. 99:961–983.
14. Kim, D., Lewis, D. L., Graziadei, L., Neer, E. J., Bar-Sagi, D. & Clapham, D. E. (1989) Nature 337:557–560.
15. Kurachi, Y., Nakajima, T., & Sugimoto, T. (1986) Pflugers Arch. 407:264–276.
16. Friel, D. D. & Bean, B. P. (1990) Pflugers Arch. 415:651–657.
17. Kurachi, Y., Ito, H., Sugimoto, T., Shimizu, T., Miki, I. & Ui, M. (1989) Pflugers Arch. 414:102–104.
18. Codina, J., Grenet, D., Yatani, A., Birnbaumer, L. & Brown, A. M. (1987) FEBS Letters, 216:104–106.
19. North, R. A., Williams, J. T., Suprenant, A. & Christie, M. J. (1987) Proc. Natl. Acad. Sci. USA 84:5487–5491.
20. Andrade, R., Malenka, R. C. & Nicoll, R. A. (1986) Science 234:1261–1265.
21. Andrade, R. & Nicoll, R. A. (1987) J. Physiol. 394:99–124.
22. VanDongen, A. M. J., Codina, J., Olate, J., Mattera, R., Joho, R., Birnbaumer, L. & Brown, A. M. (1988) Science 242:1433–1437.
23. Karschin, A., Ho, B. Y., Labarca, G., Elroy-Stein, O., Moss, B., Davidson, N. & Lester, H. A. (1991) Proc. Natl. Acad. Sci. USA 88:5694–5698.
24. Hille, B. (1992) *Ionic Channels of Excitable Membranes*, 2nd edition (Sinauer, Sunderland, Mass.).
25. Horie, M. & Irisawa, H. (1987) Am. J. Physiol. 253:H210–H214.
26. Ciani, S., Krasne, S., Myazaki, S. & Hagiwara, S. (1978) J. Membr. Biol. 44:103–134.
27. Silver, M. R. & DeCoursey, T. E. (1990) J. Gen. Physiol. 96:109–133.
28. Sentenac H., Bonneaud N., Minet M., Lacroute F., Salmon J. -M., Gaymard F. & Grignon C. (1992) Science 256:663–665.
29. Anderson J. A., Huprikar S. S., Kochian L. V., Lucas W. J. & Gaber R. F. (1992) Proc. Natl. Acad. Sci. USA 89:3736–3740.
30. Ho, K., Nichols, C. G., Lederer, W. J., Lytton, J., Vassilev, P. M., Kanazirska, M. V. & Hebert, S. C. (1993) Nature 362:31–38.
31. Kubo, Y., Baldwain, T. J., Jan, Y. N. & Jan, L. Y. (1993) Nature 362:127–132.
32. Aldrich, R. (1993) Nature 362:107–108.
33. Chomczinski, P. & Sacchi, N. (1987) Anal. Biochem. 162:156–159.
34. Dascal, N. & Lotan, I. (1992) in *Methods in Molecular Biology*, v. 13: *Protocols in Molecular Neurobiology*, eds. Longstaff, A & Revest, P. (Humana Press, Totowa, N.J.).
35. Dascal, N., Ifune, C., Hopkins, R., Snutch, T. P., Lubbert, H., Davidson, N., Simon, M., & Lester, H. A. (1986) Mol. Brain Res. 1:201–209.
36. Hoyer, D. & Schoeffer, P. (1991) J. Recept. Res. 11:197–214.
37. Barish, M. E. (1983) J. Physiol. (London) 342:309–325.
38. Dascal, N., Landau, E. M. & Lass, Y. (1984) J. Physiol. (London) 352:551–574.
39. Lubbert, H., Snutch, T. P., Dascal, N., Lester, H. A. & Davidson, N. (1987) J. Neurosci. 7:1159–1165.
40. Gilman, A. G. (1987) A. Rev. Biochem. 56:615–649.
41. Dascal, N. (1987) CRC Crit. Rev. Biochem. 22:317–387.
42. Miledi, R. & Woodward, R. M. (1989) J. Physiol. 416:601–621.
43. Lewis, D. L., Ikeda, S. R., Aryee, D. & Joho, R. H. (1991) FEBS Lett. 290:17–21.
44. Perier, F., Coulter, K. L., Radeke, C. M. & Vanderberg, C. A. (1992) J. Neurochem. 59:1971–1974.
45. Olate, J., Martinez, S., Purcell, P., Jorguera, H., Codina, J., Birnbaumer, L. & Allende, J. E. (1990) FEBS Lett. 268:27–31.

---

What is claimed is:

1. Nucleic acid comprising an isolated KGA nucleic acid encoding an inward rectifier, G-protein activated, mammalian, potassium KGA channel protein which is endogenously expressed in a mammalian cell, wherein said KGA nucleic acid is capable of hybridizing under low stringency conditions to a nucleic acid having the sequence set forth in Seq ID No:1 or its complement and wherein said KGA nucleic acid is further characterized by its ability to cause a change in potassium conductance across a Xenopus oocyte cell membrane when expressed therein.

2. The nucleic acid of claim 1 comprising RNA.
3. The nucleic acid of claim 1 comprising DNA.
4. The nucleic acid of claim 1 comprising cDNA.
5. A plasmid comprising the nucleic acid of claim 1.
6. A plasmid according to claim 6, designated pBSIIKS (−)KGA (ATCC® Accession No. 75469).
7. The nucleic acid claim 1, operatively linked to a promoter of RNA transcription.
8. A vector comprising the nucleic acid of claim 7.
9. A host vector system for the production of an inward rectifier, G-protein activated, mammalian potassium KGA channel protein which comprises the vector of claim 8 in a suitable host.
10. A host vector system of claim 9, wherein the suitable host is a bacterial cell, an insect cell, a mammalian cell, or a Xenopus oocyte.

11. A method for producing an inward rectifier, G-protein activated, mammalian potassium KGA channel protein which comprises culturing the host vector system of claim 10 under conditions permitting production of the polypeptide and recovering the polypeptide so produced.

12. An isolated nucleic acid encoding a mammalian G protein-coupled, inward-rectifying potassium channel protein, having a nucleotide sequence selected from the group consisting of:

(a) the sequence of a cDNA molecule isolated from a mammalian library, wherein the complementary strand of said cDNA molecule hybridizes under conditions of low stringency with a DNA molecule having a sequence corresponding to the sequence set forth in SEQ ID No:1, and (b) a sequence degenerate with the sequence of (a).

13. A vector comprising a nucleic acid according to claim 12.

14. A host cell transformed or transfected with a nucleic acid according to claim 12.

15. An isolated nucleic acid according to claim 12, having the nucleotide sequence of said cDNA molecule.

16. A vector comprising a nucleic acid according to claim 15.

17. A host cell transformed or transfected with a nucleic acid according to claim 15.

* * * * *

UNITED STATES PATENT AND TRADEMARK OFFICE
CERTIFICATE OF CORRECTION

PATENT NO. : 5,747,278  
DATED : May 5,1998  
INVENTOR(S) : Lester et al.

Page 1 of 2

It is certified that error appears in the above-identified patent and that said Letters Patent is hereby corrected as shown below:

Column 2, lines 2 and 15, both read "Xenopus" should read --Xenopus--.
The same occurs in column 9, line 6 and 46; column 10, lines 31 and 58; column 14, line 20.

Column 2, line 39, reads "comprises: (a)isolating", should read --comprises: (a)isolating--.

Column 2, line 61, reads "-8" should read -- -80 --. The same occurs in column 12, line 63.

Column 6, line 45, reads "(a)isolating" should read -- (a) isolating--.
Column 11, line 29, reads "MRNA" should read --mRNA--.
Column 11, line 36, reads "10 MACh" should read --10 M Ach--.

Column 12, line 20, missing a closing parenthesis which begins with"(8-OH".
Column 12, line 25, reads "-20" should read -- - -20 --.
Column 13, line 41, reads "a" should read --  --. The same occurs in column 14, line 44.

Column 13, line 54, "in co-injected with" should read --is co-injected with--.

Column 15, line 24, reference #13, reads "(ATCC " should read --(ATCC )--.
Column 23, claim 7, line 39, reads "acid claim" should read -- acid of claim --.

UNITED STATES PATENT AND TRADEMARK OFFICE
CERTIFICATE OF CORRECTION

PATENT NO.  : 5,747,278
DATED       : May 5, 1998
INVENTOR(S) : Lester et al.

It is certified that error appears in the above-identified patent and that said Letters Patent is hereby corrected as shown below:

Column 23, claim 10, line 48, reads "Xenopus" should read --Xenopus--.

Column 24, claim 12, line 31 read "CDNA" should read  -- cDNA --.

Signed and Sealed this

Eighth Day of June, 1999

Attest:

Q. TODD DICKINSON

Attesting Officer                Acting Commissioner of Patents and Trademarks

UNITED STATES PATENT AND TRADEMARK OFFICE
CERTIFICATE OF CORRECTION

PATENT NO.    : 5,747,278
DATED         : May 5, 1998
INVENTOR(S)   : Lester, et. al.

It is certified that error appears in the above-identified patent and that said Letters Patent is hereby corrected as shown below:

Column 13, line 41, "a" should read --α--.
Column 15, line 24. "13.Ito" should read --13. Ito--.
Column 23, line 37, "claim 6" should read --claim 5--.

Signed and Sealed this

Twenty-second Day of August, 2000

*Attest:*

Q. TODD DICKINSON

*Attesting Officer*            *Director of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 2076 base pairs
    ( B ) TYPE: nucleic acid
    ( C ) STRANDEDNESS: single
    ( D ) TOPOLOGY: linear ( i i ) MOLECULE TYPE: cDNA (ix) FEATURE:
 (A) NAME/KEY: CDS
 (B) LOCATION: 32..1534

(xi) SEQUENCE DESCRIPTION: SEQ ID NO:1:

```
GGCACGAGAA TCTGGATCTC CCCTCCGTAT T ATG TCT GCA CTC CGA AGG AAA              52
                                   Met Ser Ala Leu Arg Arg Lys
                                    1               5

TTT GGG GAC GAT TAC CAG GTA GTG ACC ACT TCG TCC AGC GGT TCG GGC             100
Phe Gly Asp Asp Tyr Gln Val Val Thr Thr Ser Ser Ser Gly Ser Gly
            10              15                  20

TTG CAG CCC CAG GGG CCA GGA CAG GGC CCA CAG CAG CAG CTT GTA CCC             148
Leu Gln Pro Gln Gly Pro Gly Gln Gly Pro Gln Gln Gln Leu Val Pro
        25              30              35

AAG AAG AAA CGG CAG CGG TTC GTG GAC AAG AAC GGT CGG TGC AAT GTG             196
Lys Lys Lys Arg Gln Arg Phe Val Asp Lys Asn Gly Arg Cys Asn Val
40              45              50                              55

CAG CAC GGC AAC CTG GGC AGC GAG ACC AGT CGC TAC CTT TCC GAC CTC             244
Gln His Gly Asn Leu Gly Ser Glu Thr Ser Arg Tyr Leu Ser Asp Leu
                    60              65                      70

TTC ACT ACC CTG GTG GAT CTC AAG TGG CGT TGG AAC CTC TTT ATC TTC             292
Phe Thr Thr Leu Val Asp Leu Lys Trp Arg Trp Asn Leu Phe Ile Phe
                75              80                      85

ATC CTC ACC TAC ACC GTG GCC TGG CTC TTC ATG GCG TCC ATG TGG TGG             340
Ile Leu Thr Tyr Thr Val Ala Trp Leu Phe Met Ala Ser Met Trp Trp
            90              95                  100

GTG ATC GCT TAT ACC CGG GGC GAC CTG AAC AAA GCC CAT GTC GGC AAC             388
Val Ile Ala Tyr Thr Arg Gly Asp Leu Asn Lys Ala His Val Gly Asn
        105             110             115

TAC ACT CCC TGT GTG GCC AAT GTC TAT AAC TTC CCC TCT GCC TTC CTT             436
Tyr Thr Pro Cys Val Ala Asn Val Tyr Asn Phe Pro Ser Ala Phe Leu
120             125             130                         135

TTC TTC ATC GAG ACC GAG GCC ACC ATC GGC TAT GGC TAC CGC TAC ATC             484
Phe Phe Ile Glu Thr Glu Ala Thr Ile Gly Tyr Gly Tyr Arg Tyr Ile
                    140             145                     150

ACC GAC AAG TGC CCC GAG GGC ATC ATC CTT TTC CTT TTC CAG TCC ATC             532
Thr Asp Lys Cys Pro Glu Gly Ile Ile Leu Phe Leu Phe Gln Ser Ile
                155             160             165

CTT GGC TCC ATC GTG GAC GCT TTC CTC ATC GGC TGC ATG TTC ATC AAG             580
Leu Gly Ser Ile Val Asp Ala Phe Leu Ile Gly Cys Met Phe Ile Lys
        170             175             180

ATG TCC CAG CCC AAA AAG CGC GCC GAG ACC CTC ATG TTT AGC GAG CAT             628
Met Ser Gln Pro Lys Lys Arg Ala Glu Thr Leu Met Phe Ser Glu His
        185             190             195

GCG GTT ATT TCC ATG AGG GAC GGA AAA CTC ACT CTC ATG TTC CGG GTG             676
Ala Val Ile Ser Met Arg Asp Gly Lys Leu Thr Leu Met Phe Arg Val
200             205             210                         215

GGC AAC CTG CGC AAC AGC CAC ATG GTC TCC GCG CAG ATC CGC TGC AAG             724
Gly Asn Leu Arg Asn Ser His Met Val Ser Ala Gln Ile Arg Cys Lys
                    220             225             230

CTG CTC AAA TCT CGG CAG ACA CCT GAG GGT GAG TTT CTA CCC CTT GAC             772
Leu Leu Lys Ser Arg Gln Thr Pro Glu Gly Glu Phe Leu Pro Leu Asp
                235             240             245

CAA CTT GAA CTG GAT GTA GGT TTT AGT ACA GGG GCA GAT CAA CTT TTT             820
Gln Leu Glu Leu Asp Val Gly Phe Ser Thr Gly Ala Asp Gln Leu Phe
        250             255             260

CTT GTG TCC CCT CTC ACC ATT TGC CAC GTG ATC GAT GCC AAA AGC CCC             868
Leu Val Ser Pro Leu Thr Ile Cys His Val Ile Asp Ala Lys Ser Pro
        265             270             275

TTT TAT GAC CTA TCC CAG CGA AGC ATG CAA ACT GAA CAG TTC GAG GTG             916
Phe Tyr Asp Leu Ser Gln Arg Ser Met Gln Thr Glu Gln Phe Glu Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 280 |     |     |     |     | 285 |     |     |     |     | 290 |     |     |     |     | 295 |      |
| GTC | GTC | ATC | CTG | GAA | GGC | ATC | GTG | GAA | ACC | ACA | GGG | ATG | ACT | TGT | CAA | 964  |
| Val | Val | Ile | Leu | Glu | Gly | Ile | Val | Glu | Thr | Thr | Gly | Met | Thr | Cys | Gln |      |
|     |     |     | 300 |     |     |     |     | 305 |     |     |     |     | 310 |     |     |      |
| GCT | CGA | ACA | TCA | TAC | ACC | GAA | GAT | GAA | GTT | CTT | TGG | GGT | CAT | CGT | TTT | 1012 |
| Ala | Arg | Thr | Ser | Tyr | Thr | Glu | Asp | Glu | Val | Leu | Trp | Gly | His | Arg | Phe |      |
|     |     |     | 315 |     |     |     | 320 |     |     |     |     | 325 |     |     |     |      |
| TTC | CCT | GTA | ATT | TCT | TTA | GAA | GAA | GGA | TTC | TTT | AAA | GTC | GAT | TAC | TCC | 1060 |
| Phe | Pro | Val | Ile | Ser | Leu | Glu | Glu | Gly | Phe | Phe | Lys | Val | Asp | Tyr | Ser |      |
|     |     | 330 |     |     |     |     | 335 |     |     |     | 340 |     |     |     |     |      |
| CAG | TTC | CAT | GCA | ACC | TTT | GAA | GTC | CCC | ACC | CCT | CCG | TAC | AGT | GTG | AAA | 1108 |
| Gln | Phe | His | Ala | Thr | Phe | Glu | Val | Pro | Thr | Pro | Pro | Tyr | Ser | Val | Lys |      |
|     | 345 |     |     |     |     | 350 |     |     |     |     | 355 |     |     |     |     |      |
| GAG | CAG | GAA | GAA | ATG | CTT | CTC | ATG | TCT | TCC | CCT | TTA | ATA | GCA | CCA | GCC | 1156 |
| Glu | Gln | Glu | Glu | Met | Leu | Leu | Met | Ser | Ser | Pro | Leu | Ile | Ala | Pro | Ala |      |
| 360 |     |     |     |     | 365 |     |     |     |     | 370 |     |     |     |     | 375 |      |
| ATA | ACC | AAC | AGC | AAA | GAA | AGA | CAC | AAT | TCT | GTG | GAG | TGC | TTA | GAT | GGA | 1204 |
| Ile | Thr | Asn | Ser | Lys | Glu | Arg | His | Asn | Ser | Val | Glu | Cys | Leu | Asp | Gly |      |
|     |     |     |     | 380 |     |     |     |     | 385 |     |     |     |     | 390 |     |      |
| CTA | GAT | GAC | ATT | AGC | ACA | AAA | CTT | CCA | TCG | AAG | CTG | CAG | AAA | ATT | ACG | 1252 |
| Leu | Asp | Asp | Ile | Ser | Thr | Lys | Leu | Pro | Ser | Lys | Leu | Gln | Lys | Ile | Thr |      |
|     |     |     | 395 |     |     |     |     | 400 |     |     |     |     | 405 |     |     |      |
| GGG | AGA | GAA | GAC | TTT | CCC | AAA | AAA | CTC | CTG | AGG | ATG | AGT | TCT | ACA | ACT | 1300 |
| Gly | Arg | Glu | Asp | Phe | Pro | Lys | Lys | Leu | Leu | Arg | Met | Ser | Ser | Thr | Thr |      |
|     |     | 410 |     |     |     |     | 415 |     |     |     |     | 420 |     |     |     |      |
| TCA | GAA | AAA | GCC | TAT | AGT | TTG | GGT | GAT | TTG | CCC | ATG | AAA | CTC | CAA | CGA | 1348 |
| Ser | Glu | Lys | Ala | Tyr | Ser | Leu | Gly | Asp | Leu | Pro | Met | Lys | Leu | Gln | Arg |      |
|     | 425 |     |     |     |     | 430 |     |     |     |     | 435 |     |     |     |     |      |
| ATA | AGT | TCG | GTT | CCT | GGC | AAC | TCT | GAA | GAA | AAA | CTG | GTA | TCT | AAA | ACC | 1396 |
| Ile | Ser | Ser | Val | Pro | Gly | Asn | Ser | Glu | Glu | Lys | Leu | Val | Ser | Lys | Thr |      |
| 440 |     |     |     |     | 445 |     |     |     |     | 450 |     |     |     |     | 455 |      |
| ACC | AAG | ATG | TTA | TCA | GAT | CCC | ATG | AGC | CAG | TCT | GTG | GCC | GAT | TTG | CCA | 1444 |
| Thr | Lys | Met | Leu | Ser | Asp | Pro | Met | Ser | Gln | Ser | Val | Ala | Asp | Leu | Pro |      |
|     |     |     |     | 460 |     |     |     |     | 465 |     |     |     |     | 470 |     |      |
| CCG | AAG | CTT | CAA | AAG | ATG | GCT | GGA | GGA | CCT | ACC | AGG | ATG | GAA | GGG | AAT | 1492 |
| Pro | Lys | Leu | Gln | Lys | Met | Ala | Gly | Gly | Pro | Thr | Arg | Met | Glu | Gly | Asn |      |
|     |     |     | 475 |     |     |     |     | 480 |     |     |     |     | 485 |     |     |      |
| CTT | CCA | GCC | AAA | CTA | AGA | AAA | ATG | AAC | TCT | GAC | CGC | TTC | ACA |     |     | 1534 |
| Leu | Pro | Ala | Lys | Leu | Arg | Lys | Met | Asn | Ser | Asp | Arg | Phe | Thr |     |     |      |
|     |     | 490 |     |     |     |     | 495 |     |     |     |     | 500 |     |     |     |      |

| | |
|---|---|
| TAGCAAAACA CCCCATTAGG CATTATTTCA TGTTTTGATT TAGTTTTAGT CCAATATTTG | 1594 |
| GCTGATAAGA TAATCCTCCC CGGGAAATCT GAGAGGTCTA TCCCAGTCTG GCAAATTCAT | 1654 |
| CAGAGGACTC TTCATTGAAG TGTTGTTACT GTGTTGAACA TGAGTTACAA AGGGAGGACA | 1714 |
| TCATAAGAAA GCTAATAGTT GGCATGTATT ATCACATCAA GCATGCAATA ATGTGCAAAT | 1774 |
| TTTGCATTTA GTTTCTGGC ATGATTTATA TATGGCATAT TTATATTGAA TATTCTGGAA | 1834 |
| AAATATATAA ATATATATTT GAAGTGGAGA TATTCTCCCC ATAATTTCTA ATATATGTAT | 1894 |
| TAAGCCAAAC ATGAGTGGAT AGCTTTCAGG GCACTAAAAT AATATACATG CATACATACA | 1954 |
| TACATGCATA TGCACAGACA CATACACACA CATACTCATA TATATAAAAC ATACCCATAC | 2014 |
| AAACATATAT ATCTAATAAA AATTGTGATG TTTTGTTCAA AAAAAAAAAA AAAAACTCG | 2074 |
| AG | 2076 |

( 2 ) INFORMATION FOR SEQ ID NO:2:

( i ) SEQUENCE CHARACTERISTICS:
( A ) LENGTH: 501 amino acids
( B ) TYPE: amino acid (D) TOPOLOGY: linear (ii) MOLECULE TYPE: protein (xi) SEQUENCE DESCRIPTION: SEQ ID NO:2:

```
Met Ser Ala Leu Arg Arg Lys Phe Gly Asp Asp Tyr Gln Val Val Thr
 1               5                  10                  15

Thr Ser Ser Ser Gly Ser Gly Leu Gln Pro Gln Gly Pro Gly Gln Gly
                20                  25                  30

Pro Gln Gln Gln Leu Val Pro Lys Lys Arg Gln Arg Phe Val Asp
                35              40                  45

Lys Asn Gly Arg Cys Asn Val Gln His Gly Asn Leu Gly Ser Glu Thr
         50                  55                  60

Ser Arg Tyr Leu Ser Asp Leu Phe Thr Thr Leu Val Asp Leu Lys Trp
 65                  70                  75                  80

Arg Trp Asn Leu Phe Ile Phe Ile Leu Thr Tyr Thr Val Ala Trp Leu
                85                  90                  95

Phe Met Ala Ser Met Trp Trp Val Ile Ala Tyr Thr Arg Gly Asp Leu
                100                 105                 110

Asn Lys Ala His Val Gly Asn Tyr Thr Pro Cys Val Ala Asn Val Tyr
            115                 120                 125

Asn Phe Pro Ser Ala Phe Leu Phe Phe Ile Glu Thr Glu Ala Thr Ile
    130                 135                 140

Gly Tyr Gly Tyr Arg Tyr Ile Thr Asp Lys Cys Pro Glu Gly Ile Ile
145                 150                 155                 160

Leu Phe Leu Phe Gln Ser Ile Leu Gly Ser Ile Val Asp Ala Phe Leu
                165                 170                 175

Ile Gly Cys Met Phe Ile Lys Met Ser Gln Pro Lys Lys Arg Ala Glu
            180                 185                 190

Thr Leu Met Phe Ser Glu His Ala Val Ile Ser Met Arg Asp Gly Lys
            195                 200                 205

Leu Thr Leu Met Phe Arg Val Gly Asn Leu Arg Asn Ser His Met Val
    210                 215                 220

Ser Ala Gln Ile Arg Cys Lys Leu Leu Lys Ser Arg Gln Thr Pro Glu
225                 230                 235                 240

Gly Glu Phe Leu Pro Leu Asp Gln Leu Glu Leu Asp Val Gly Phe Ser
                245                 250                 255

Thr Gly Ala Asp Gln Leu Phe Leu Val Ser Pro Leu Thr Ile Cys His
            260                 265                 270

Val Ile Asp Ala Lys Ser Pro Phe Tyr Asp Leu Ser Gln Arg Ser Met
    275                 280                 285

Gln Thr Glu Gln Phe Glu Val Val Val Ile Leu Glu Gly Ile Val Glu
290                 295                 300

Thr Thr Gly Met Thr Cys Gln Ala Arg Thr Ser Tyr Thr Glu Asp Glu
305                 310                 315                 320

Val Leu Trp Gly His Arg Phe Phe Pro Val Ile Ser Leu Glu Glu Gly
                325                 330                 335

Phe Phe Lys Val Asp Tyr Ser Gln Phe His Ala Thr Phe Glu Val Pro
            340                 345                 350

Thr Pro Pro Tyr Ser Val Lys Glu Gln Glu Glu Met Leu Leu Met Ser
    355                 360                 365

Ser Pro Leu Ile Ala Pro Ala Ile Thr Asn Ser Lys Glu Arg His Asn
    370                 375                 380

Ser Val Glu Cys Leu Asp Gly Leu Asp Asp Ile Ser Thr Lys Leu Pro
385                 390                 395                 400
```

-continued

| Ser | Lys | Leu | Gln | Lys 405 | Ile | Thr | Gly | Arg | Glu 410 | Asp | Phe | Pro | Lys | Lys 415 | Leu |
| --- | --- | --- | --- | --- | --- | --- | --- | --- | --- | --- | --- | --- | --- | --- | --- |
| Leu | Arg | Met | Ser 420 | Ser | Thr | Thr | Ser | Glu 425 | Lys | Ala | Tyr | Ser | Leu 430 | Gly | Asp |
| Leu | Pro | Met 435 | Lys | Leu | Gln | Arg | Ile 440 | Ser | Ser | Val | Pro | Gly 445 | Asn | Ser | Glu |
| Glu | Lys 450 | Leu | Val | Ser | Lys | Thr 455 | Thr | Lys | Met | Leu | Ser 460 | Asp | Pro | Met | Ser |
| Gln 465 | Ser | Val | Ala | Asp | Leu 470 | Pro | Pro | Lys | Leu | Gln 475 | Lys | Met | Ala | Gly | Gly 480 |
| Pro | Thr | Arg | Met | Glu 485 | Gly | Asn | Leu | Pro | Ala 490 | Lys | Leu | Arg | Lys | Met 495 | Asn |
| Ser | Asp | Arg | Phe 500 | Thr | | | | | | | | | | | |